US011013940B1

United States Patent

Case et al.

(12) United States Patent
(10) Patent No.: US 11,013,940 B1
(45) Date of Patent: May 25, 2021

(54) SCBA MASK SHIELD

(71) Applicants: Patric Case, Sparks, NV (US); Cody Cavin, Sparks, NV (US)

(72) Inventors: Patric Case, Sparks, NV (US); Cody Cavin, Sparks, NV (US)

(73) Assignee: C&C Design Ltd., Sparks, NV (US)

( * ) Notice: Subject to any disclaimer, the term of this patent is extended or adjusted under 35 U.S.C. 154(b) by 750 days.

(21) Appl. No.: 15/600,133

(22) Filed: May 19, 2017

Related U.S. Application Data

(60) Provisional application No. 62/341,829, filed on May 26, 2016.

(51) Int. Cl.
*A62B 25/00* (2006.01)
*A62B 18/08* (2006.01)
(Continued)

(52) U.S. Cl.
CPC ................ *A62B 25/00* (2013.01); *A61F 9/04* (2013.01); *A62B 18/02* (2013.01); *A62B 18/082* (2013.01)

(58) Field of Classification Search
CPC ....... A62B 18/00; A62B 18/02; A62B 18/025; A62B 18/04; A62B 18/06; A62B 18/08;
(Continued)

(56) References Cited

U.S. PATENT DOCUMENTS 4,069,516 A 1/1978 Watkins, Jr.
4,076,373 A * 2/1978 Moretti .................. A61F 9/025 359/507

(Continued)

FOREIGN PATENT DOCUMENTS

CA 2308086 A1 * 11/2001 ............... A42B 3/22
DE 202019004041 U1 * 1/2020 ............... A42B 3/04
WO WO-2015044624 A1 * 4/2015 ............. A42B 3/006

OTHER PUBLICATIONS

"555 Fitness Shields", retrieved from https://555fitness.com/collections/accessories/products/555-fitness-shields (Year: 2020).*

(Continued)

*Primary Examiner* — Joseph D. Boecker
(74) *Attorney, Agent, or Firm* — Merchant & Gould P.C.

(57) ABSTRACT

A protective shield is provided for covering a self-contained breathing apparatus (SCBA) mask or a full-face air purifying respirator (APR) lens to prevent damage and scratching. The shield consists of a die cut shape of thermoplastic sheet that duplicates the outline of the self-contained breathing apparatus mask lens and/or frame. The protective shield can be produced using various grades, colors and/or densities of material replicating limited visibility or blackout conditions. To protect the majority of the plastic lens, the shape of the shield includes a peripheral overlap onto the mask utilizing the SCBA lens frame. The shield can be attached to the self-contained breathing apparatus face mask by means of any of the following: bungee, hook, or elastic cord; all of which allows the shield to be attached or removed quickly. Many SCBA/APR training exercises require limited visibility. The invention can be used as an effective training tool to prevent light transmission and simulate extremely limited visibility.

11 Claims, 7 Drawing Sheets

(51) Int. Cl.
*A62B 18/02* (2006.01)
*A61F 9/04* (2006.01)

(58) Field of Classification Search
CPC ..... A62B 18/082; A62B 18/084; A62B 99/00; A62B 25/00; A42B 3/18; A42B 3/185; A42B 3/20; A42B 3/22; A42B 3/225; A42B 3/226; A42B 3/227; A42B 3/228; A42B 3/24; A42B 3/26; A42B 3/00; A42B 3/28; A42B 3/288; A61F 9/04; A61F 9/045; A61F 9/06; A61F 9/061; A61F 9/062; A61F 9/064; A61F 9/065; A61M 16/06; A62C 99/0081
USPC .................................................. D29/109, 110
See application file for complete search history.

(56) References Cited

U.S. PATENT DOCUMENTS

| | | | | | | |
|---|---|---|---|---|---|---|
| 4,473,370 | A | * | 9/1984 | Weiss | A61F 9/00 | 604/294 |
| 4,689,058 | A | * | 8/1987 | Vogt | B01D 39/163 | 55/486 |
| 5,080,092 | A | | 1/1992 | Tenna | | |
| 5,155,863 | A | * | 10/1992 | Roberts | A61F 9/029 | 128/202.13 |
| 5,671,483 | A | * | 9/1997 | Reuber | A42B 3/245 | 2/424 |
| 6,062,222 | A | | 5/2000 | Lewis et al. | | |
| 6,347,401 | B1 | | 2/2002 | Joyce | | |
| 6,687,910 | B1 | * | 2/2004 | Smallwood | A62C 99/0081 | 2/10 |
| 2005/0251890 | A1 | * | 11/2005 | Landis | A61F 9/022 | 2/9 |
| 2006/0096012 | A1 | * | 5/2006 | De Grunwald | A42B 3/24 | 2/424 |

OTHER PUBLICATIONS

"MASKhaze", retrieved from https://www.maskhaze.com/shop-1 (Year: 2020).*

* cited by examiner

SCBA MASK SHIELD

CROSS REFERENCE TO RELATED APPLICATIONS

The present application includes the disclosure of U.S. provisional application Ser. No. 62/341,829 that was filed with the United States Patent and Trademark Office on May 26, 2016. A priority right is claimed to U.S. application Ser. No. 62/341,829 to the extent appropriate. The complete disclosure of U.S. application Ser. No. 62/341,829 is incorporated herein by reference.

FIELD OF THE DISCLOSURE

The present disclosure is directed at self-contained breathing apparatus (SCBA) or air purifying respirator (APR) mask protective shields in general. More specifically, the present disclosure is directed to a shield which can be attached over a self-contained breathing apparatus frame or lens that is easily removed by the user. The shield may or may not obscure or completely inhibit vision for training purposes.

BACKGROUND

In order to enter buildings and structures that are on fire and filled with smoke, firefighters typically utilize a self-contained breathing apparatus along with protective clothing. An extremely important piece of the ensemble of personal protective equipment (PPE) is the SCBA face piece or mask. Since high visibility is the goal of the apparatus manufacturer's, considerable effort has been taken to make the mask lens as large as possible and configured for maximum visual perception. Lenses on the mask are made to withstand considerable forces to prevent cracking, shattering, and breaking but are still not impervious to scratches, abrasions or moderate damage that can impede and reduce the user's vision.

While no prior art has been found consistent with the application of the invention listed, below are patents that display some relevance to which listed invention (shield) may be applied, i.e. defining SCBA and APR mask.

| U.S. Pat. No. | Inventor | Issue Date |
|---|---|---|
| 4,069,516 | Watkins Jr. | Jan. 24, 1978 |
| 5,080,092 | Tenna | Jan. 14, 1992 |
| 5,155,863 | Roberts | Oct. 20, 1992 |
| 6,062,222 | Lewis et al. | May 16, 2000 |
| 6,347,401 | Joyce | Feb. 19, 2002 |
| 6,687,910 | Smallwood | Feb. 10, 2004 |

U.S. Pat. No. 4,069,516 issued to Watkins Jr. is for a resilient flexible sealing element conformable to the face of a wearer supported by a mask body. The sealing element extends completely around the open side of the mask body with a hinge web having a bead extending along the opposite sides and across the top of the mask for controlled buckling of the web in a manner mechanically loading the face engaging sealing element.

U.S. Pat. No. 5,080,092 issued to Tenna describes a protective mask that has a face shield covering the user's face formed of a rigid transparent material rimmed by a bellows seal. The seal provides the necessary tightness with comfort allowing continuous use of the mask even over an extended length of time.

Roberts and U.S. Pat. No. 5,155,863 teaches a removable cover for an SCBA mask lens made from a fabric sheet with an elastic band that stretches over the frame of an SCBA mask to secure it in place. This cover can also be used as a 'blackout mask' to simulate low to no visibility for training exercises.

Lewis et al in U.S. Pat. No. 6,062,222 discloses a face mask for a self-contained breathing apparatus that has two pairs of straps fixed to the frame and a net head piece. The straps at the top of the head piece are fixed and the bottom straps are adjustable. A nose cup includes ribs that receive legs of a mounting member for eyeglasses. The mounting member moves relevant to the user's eyes.

Joyce in U.S. Pat. No. 6,347,401 teaches a thin protective sheet for covering a face plate on an air mask. This invention may comprise a substantially rectangular thin sheet of plastic having two circular cut outs and square cut outs with an edge having a semi-circular shape. Other embodiments may have a series of curves or oval shapes to fit around the mask protecting the mask from scratches, nicks, scrapes or any other damage from use.

U.S. Pat. No. 6,687,910 pertains to a thermoplastic mold, which can be placed on an SCBA face piece for methods of training by utilizing a semi-translucent or opaque material to cover a mask to simulate a smoke filled environment. The cover is attached using tape or Velcro.

SUMMARY

Self-contained breathing apparatus are used to supply air to the user in what is defined as immediately dangerous to life and health (IDLH) environments. Air purifying respirators differ by using a cartridge filter, commonly recognized as a "gas mask." The difference in the two systems is SCBA uses supplied "clean" air, and an APR filters particulates from the environment. However, both systems commonly use to the same mask where SCBA and APR functions may be interchangeable.

The masks described above are being manufactured with fields of view and visibility as high priority items. Clear vision assists with accomplishing the task set out by the wearer more efficiently and quickly, both attributes are important in (sometimes) life threatening conditions. Often times tasks carried out by the user are physical and dirty, and as such, personal protective equipment is more likely to be damaged while working. Often, due to limited visibility and limited air supply in an SCBA, the mask is only used for short periods of time on the face; however, the mask must always accompany the person it is assigned to. This means the mask must many times be attached, clipped, strapped, or harnessed to a part of said person or his/her PPE ensemble. This subjects the mask and its components to scratching, shattering, accumulating debris and other damage to the lens. Once the lens is scratched or damaged, depending on the manufacturer's recommendations, the mask is to be discarded and replaced, or the lens removed and replaced. Either scenario results in an undue expense for the department or company issuing the equipment.

Therefore, it is a primary objective of the invention to protect the lens of a mask from above mentioned damage while the user is not wearing the mask on their face. This object is realized by the use of a shield that is configured to fit on the outside of the self-contained breathing apparatus mask lens. The shield can slightly overlap the face mask lens preventing possibility of the lens coming in contact with foreign objects that may scratch or otherwise damage the lens, and is held in place with elastic cording, elastic straps and/or pressure fitted tabs/hooks around the mask. It may be clearly seen that this system of protection allows for an efficient and effective way to guard the lens from damage while not in use.

This shield can be easily attached to the exterior of the mask lens, using elastic cord or the like, or be molded to form around the lens frame at specific points with some flexibility in the shield allowing it to snap on and off of the mask with ease.

Previously, mask bags have been an efficient way of keeping the mask out of the elements and as a means of protection. Mask bags however cannot eliminate scratching of the lens as the fabric or material used is constantly moving against the face of the lens and if even minor debris is introduced into the bag, its effectiveness is greatly reduced. Bags also don't protect against penetrating or blunt impact. The addition of the bag being clipped to the user's SCBA harness or person also adds bulk, which may impede the user's ability to function efficiently. Once the mask is placed on the user and is being used as intended (per manufacturer), the bag is then often discarded, as there is nowhere to store the bag. In the case of firefighting, the bags are often times not rated for the heat that may be encountered while fighting fire.

Self-contained breathing apparatus have been used in conjunction with smoke filled rooms for training firefighters. Firefighters, through the course of their job, are required to operate and function in limited to zero visibility and do so effectively. A secondary object of this invention is to provide the user with a piece of equipment that not only protects the user's equipment, but also affords the ability to simulate a smoke filled room. Smoke filled rooms for training are often times difficult to attain as it requires extra equipment such as smoke generators, and a relatively small space that smoke can be introduced into. Added costs to fire departments are the generators themselves, as well as smoke fluid which is consumed and needs to be continually purchased to train personnel.

Currently departments are utilizing cloth placed over the masks or opaque plastic sheets on the inside of the mask to simulate limited visibility. The downside to cloth is that it can tear, rip, stain, and the user can still partially see through it. Also, should something go wrong with the training evolution, the user must remove their helmet and then remove the cloth, which can be cumbersome. Shields that are placed inside the mask require the user to remove PPE almost completely to insert or remove the visibility limitation device, resulting in decreased productivity.

The shield can be produced in a varying levels of translucency or in its base color of black which provides nearly complete obstruction of view, allowing the user to learn how to function in full PPE without altering the feeling of the equipment, making for a more realistic training. The shield's ability to be easily and intuitively attached to the outside of the mask without removal of PPE means that training can be conducted more efficiently.

Another object of the invention is its adaptability to be used with different manufacturer's equipment. Each SCBA maker makes a different style of mask; therefore, the shield may be specifically configured to fit every style, as only a different template is required to duplicate each shape. Most commonly used equipment by firefighting agencies are Scott, Survivair, MSA, Draeger and Avon.

A shield for covering an exterior surface of a lens on a mask is described. The shield includes: a cover having an inside surface, an outside surface, a perimeter corresponding to a perimeter of the lens or corresponding to a perimeter of a frame holding the lens, and a contour configured to follow a contour of the lens; a separation member located on the inside surface of the cover and constructed to provide separation between the lens and the cover when the cover is located covering the lens; and an elastic cord extending from the cover and constructed to hold the cover to the mask so that the cover is located covering the lens.

A combination mask and shield is described. The combination mask and shield includes: a mask provided as part of a self-contained breathing apparatus and including a lens and a frame holding the lens in place; and a shield constructed to cover an exterior surface of the lens, the shield comprising: a cover having an inside surface, an outside surface, a perimeter for responding to a perimeter of the lens or corresponding to a perimeter of the frame, and a contour configured to follow the contour of the lens; a separation member located on the inside surface of the cover and providing separation between the lens and the cover; and a first elastic cord extending from a first part of the cover and a second elastic cord extending from the second part of the cover, and wherein the first elastic cord and the second elastic cord interact with the mask to hold the shield over the lens.

A method of manufacturing a shield for covering an exterior surface of a lens on a mask is described. The method includes steps of: die cutting a plastic material and forming the plastic material so that the formed plastic material has shape corresponding to a shape of a lens on a mask provided as part of a self-contained breathing apparatus, wherein the formed plastic material has an inside surface, an outside surface, and a perimeter; locating a separation member on the inside surface of the formed plastic material, wherein the separation member is constructed to provide separation between the lens and the formed plastic material when the cover is located covering the lens; and attaching an elastic cord to the formed plastic material, wherein the elastic cord is constructed to hold the formed plastic material to the mask when the formed plastic material is located covering the lens.

A shield for covering an exterior surface of a lens on a mask is described. The method includes: a cover having an inside surface, an outside surface, a perimeter corresponding to a perimeter of the lens or corresponding to a perimeter of a frame holding the lens, and a contour configured to follow a contour of the lens; a separation member located on the inside surface of the cover and constructed to provide separation between the lens and the cover when the cover is located covering the lens; and a hook construction extending from a right side and from a left side of the cover along the perimeter and constructed to wrap around a portion of a mask frame that holds the lens in place to hold the cover to the mask.

DETAILED DESCRIPTION

Figure 1:
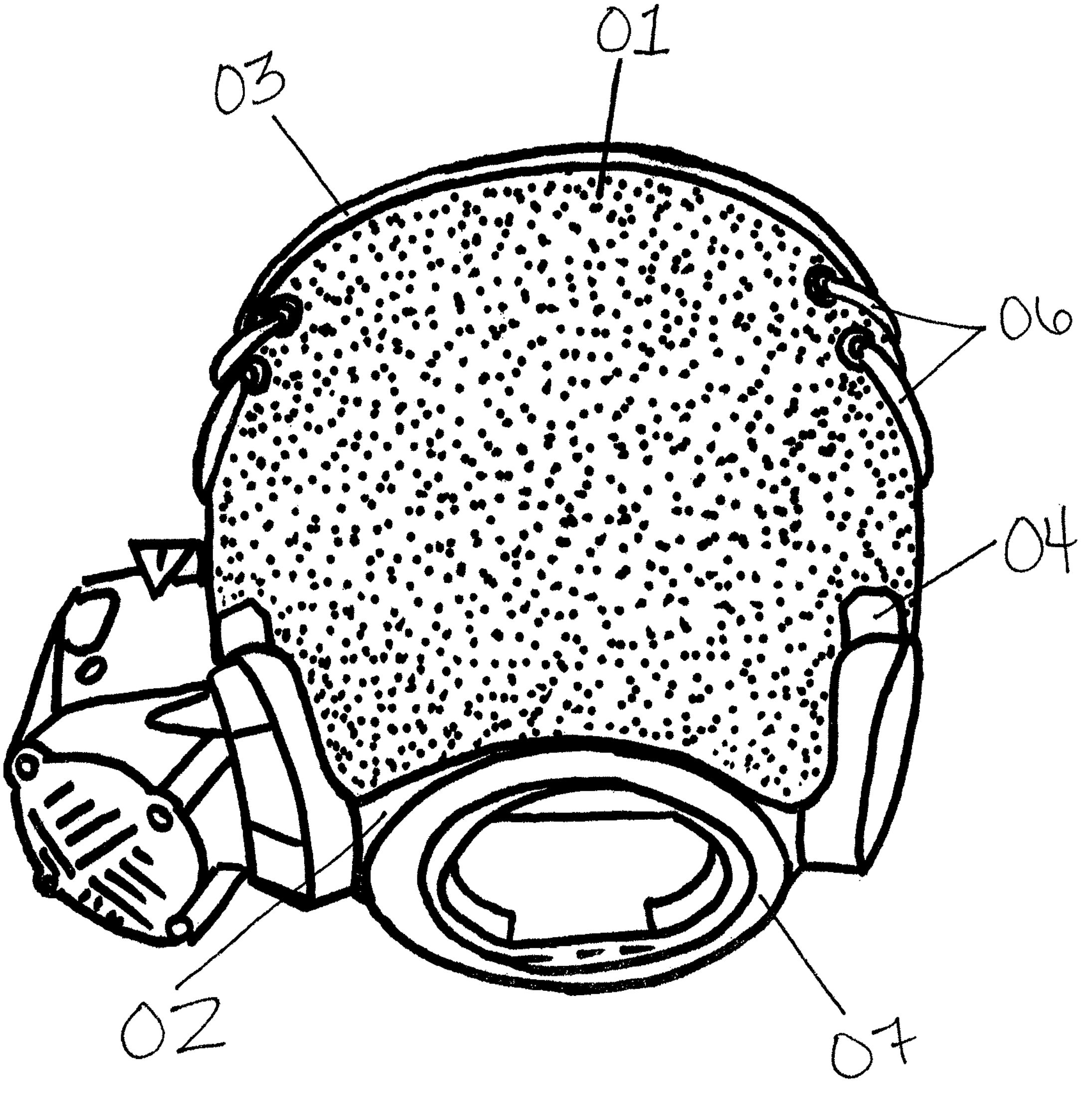
FIG. 1 is a perspective front and bottom view of a commercially manufactured mask with voice emitter and with the shield attached thereto according to the principles of the present invention.
Figure 2:
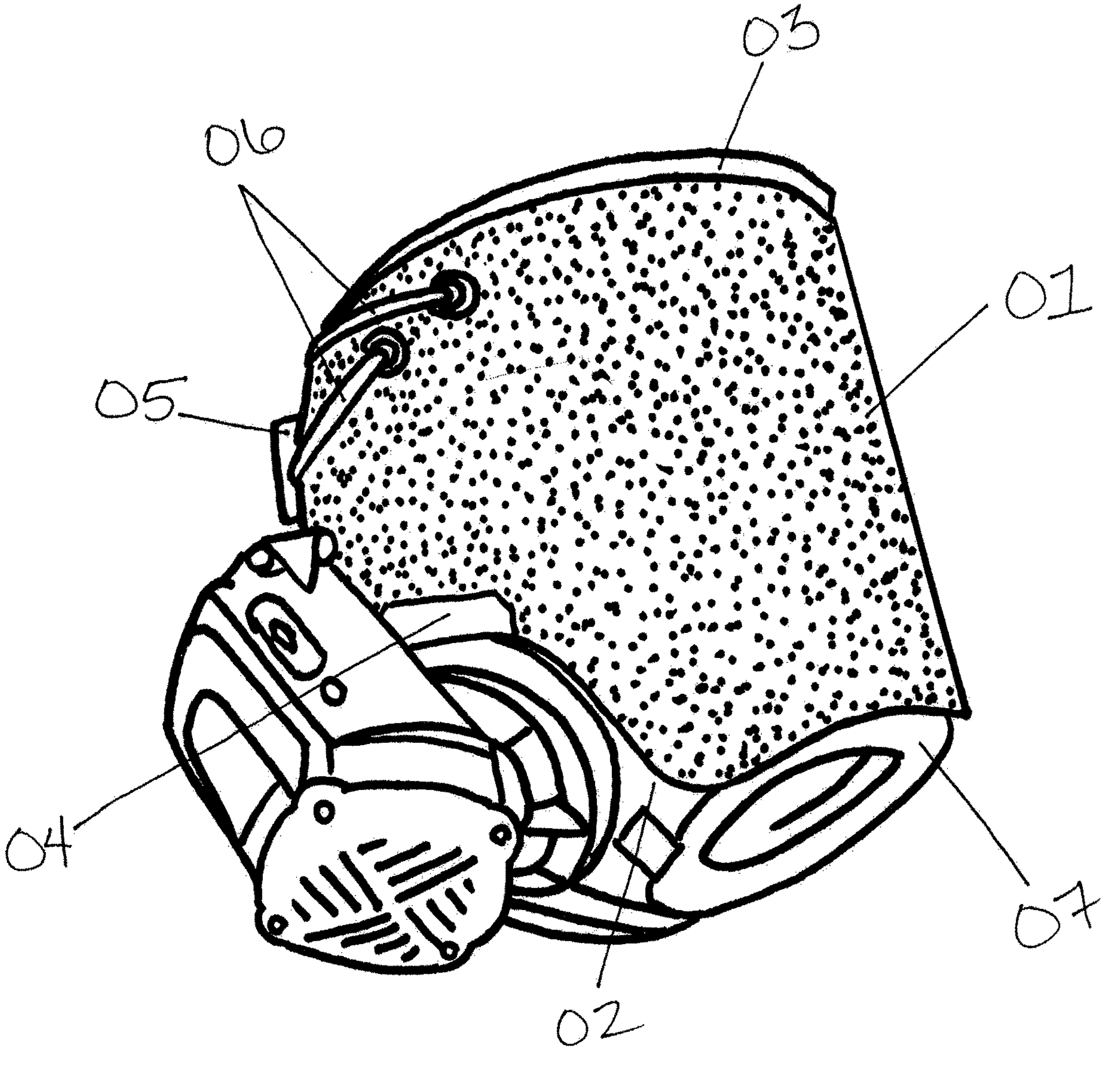
FIG. 2 is a perspective side and bottom view of the combination mask and shield according to FIG. 1.

The shield, the combination mask and shield, and the method of manufacturing and using the shield are described with reference to FIGS. 1-8. A shield 01 is shown covering a self-contained breathing apparatus (SCBA), self contained underwater breathing apparatus, gas mask or any other respiratory protection mask lens 02 and/or frame 03. The shield 01 is used for scratch and impact protection of the lens while the mask 07 is not in use and could be used for black-out or limited visibility training exercises for firefighters, SCUBA divers, police, military, etc. The shield 01 is 100 percent light blocking material or translucent material and has a shape that simulates the outline or frame 03 of the self contained breathing apparatus, self contained underwater breathing apparatus or gas mask lens 02 and/or frame 03. On the inside of the shield 08, around the outside edges, there is a felt, suede, rubber, etc. strip 04 to raise the shield slightly off the frame 03 and lens 02 of the mask 07 as to prevent any contact with the main viewing area of the mask lens 02. As there are numerous original equipment manufacturers of the breathing apparatus/respiratory protection (mask 07), the drawings illustrate only one mask, which represents a very common device in domestic and professional usage. The mask 07 of FIGS. 1-6 is an exemplary mask made by Scott in the Scott-AV-3000 model. It will be realized that there are many more models available and normally each are offered in small, medium, and large sizes. It will be appreciated that the shield according to the invention can be modified with slight variations to accommodate the various masks available on the market and sizes. It is additionally noted that the SCBA mask illustrated in the figures is provided without a rubber face seal that is required for the mask to function properly. One would understand that the mask would include the rubber face seal during operation.

In a preferred embodiment, the shield 01 is formed of rigid thermoplastic (such as Kydex) or injection-molded plastic to a thickness of 1 to 15 millimeters, however other types and sizes of thermoplastic would be acceptable substitutes such as polyethylene, cellulose acetate, polycarbonate, acrylic, acetyl or polyester etc. An exemplary method of manufacturer is to die cut the shield 01 to a shape duplicating or following the outline of the mask and/or frame 03.

As stated above, the shield 01 may or may not have light penetration density concentration. This light penetration density is achieved using a process consisting of silk screening, lithography, flexography, or rotography etc., coating the surface of the parent thermoplastic material of the shield 01 with any mixture of any color ink.

It should not be overlooked that the base thermoplastic or injection-molded material may be produced with the color integrally formed during the manufacturing process by formulating a predetermined mixture of any color ink and transparent additives.

The shape of the shield 01 may include some overlap onto the mask frame 03 to preclude most light penetration. Some light leakage around the periphery is not problematic since the main purpose of the shield 01 would be lens 02 protection, and using the product for training would be a secondary benefit. The overlap of the shield 01 on the frame 03 can be non-existent or it can cover any portion of the frame 03 of the mask 07 including 100 percent coverage.

Figure 4:
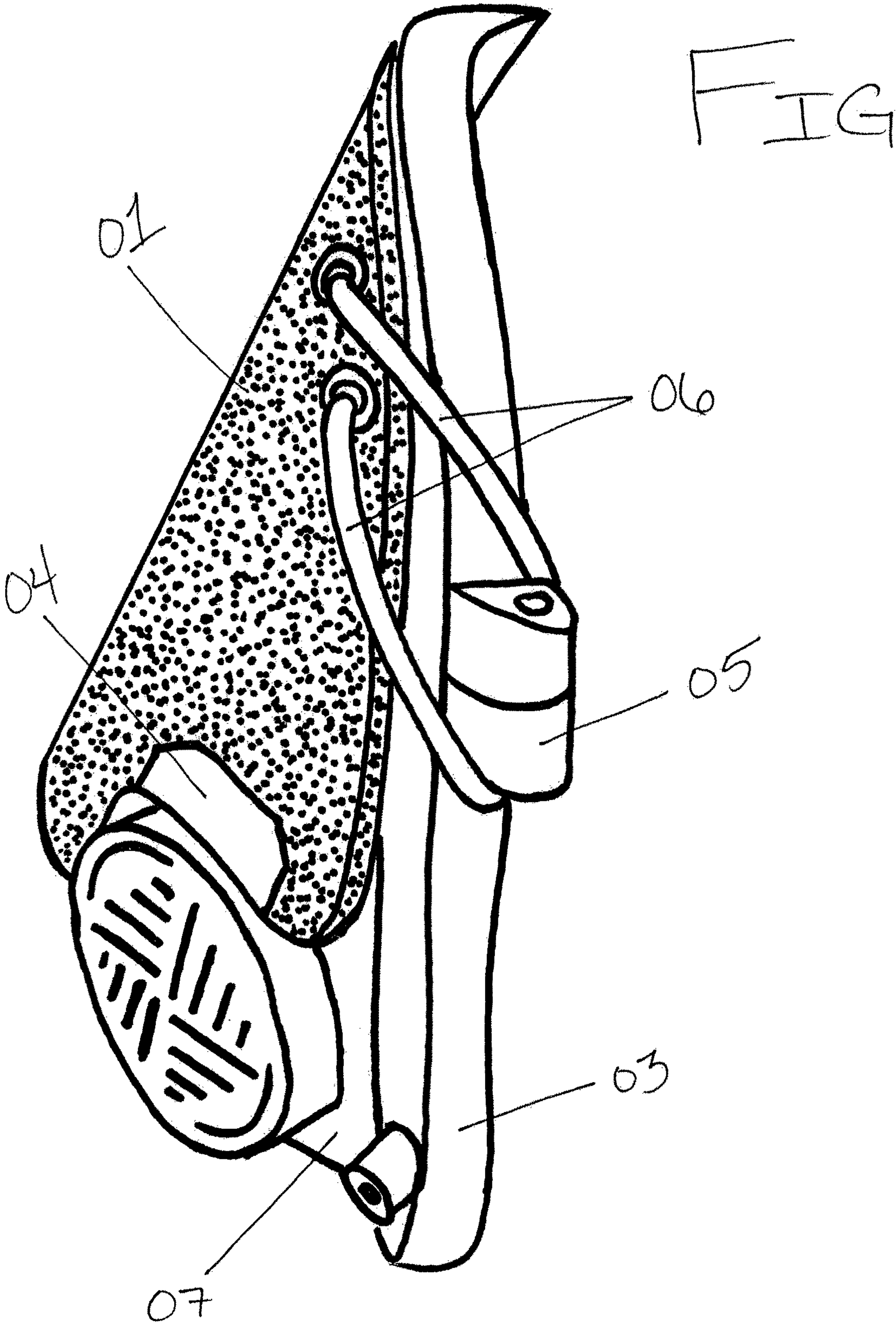
FIG. 4 is a rear and side view of the combination mask and shield according to FIG. 1.
Figure 5:
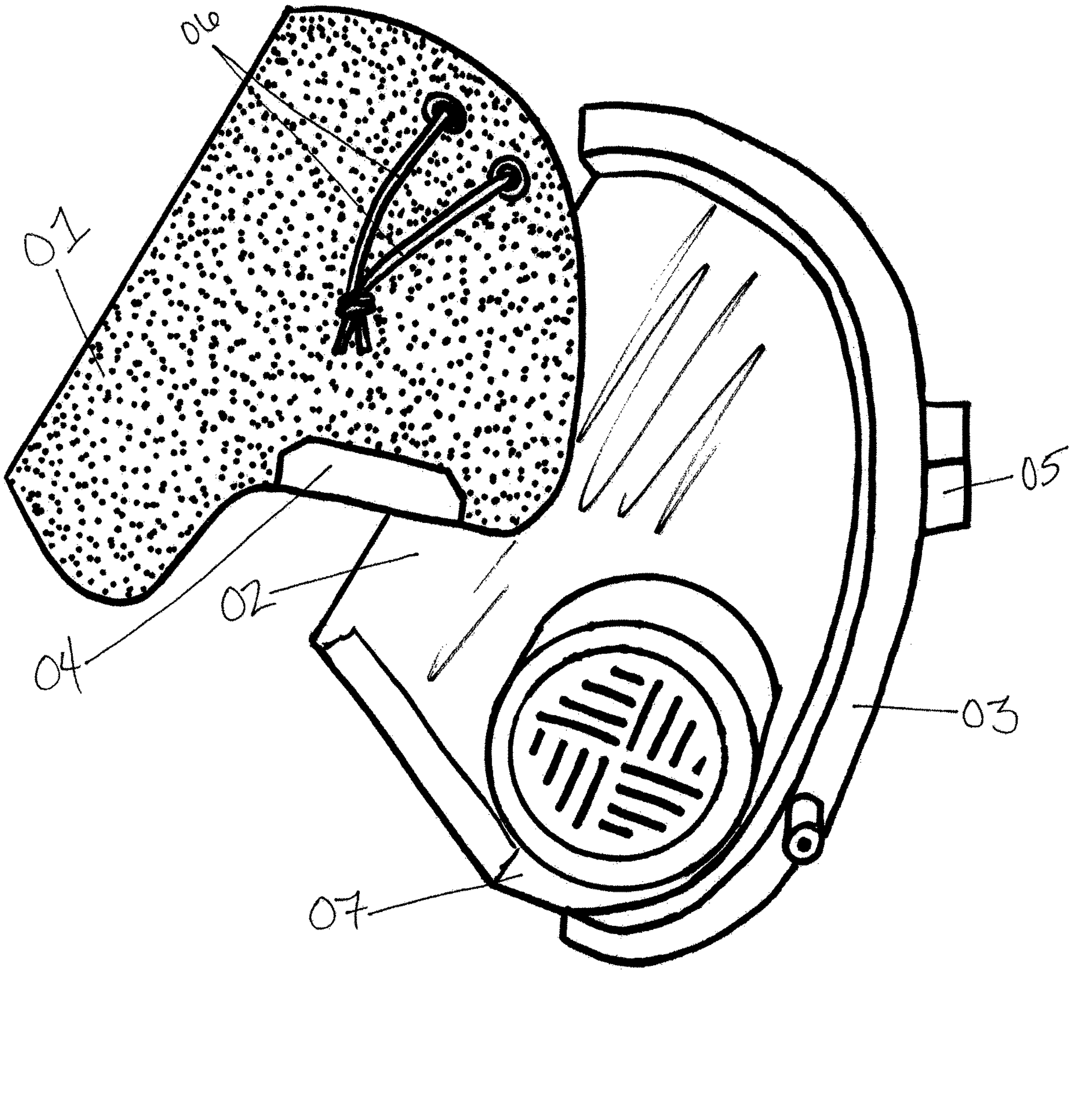
FIG. 5 is a side exploded view of the combination mask and shield according to FIG. 1.
Figure 6:
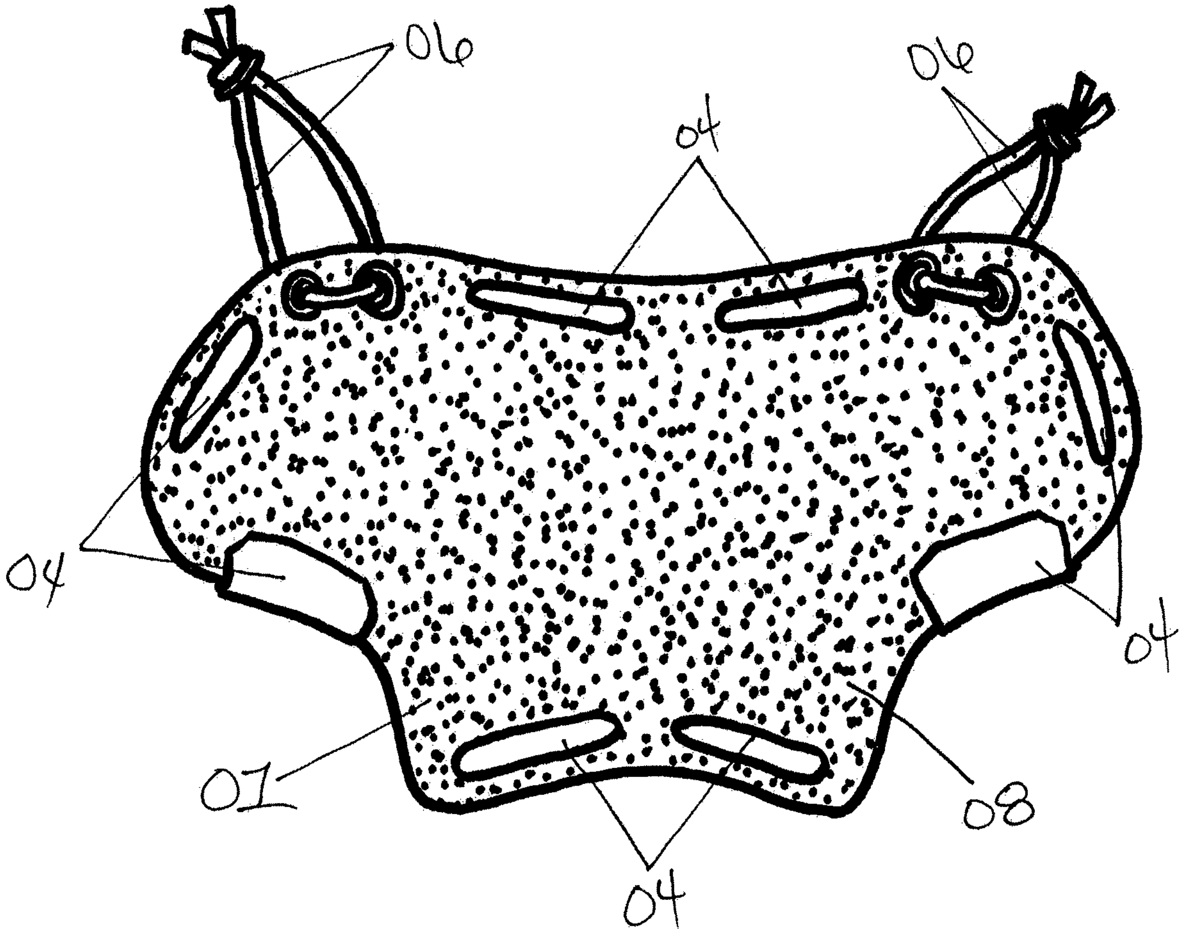
FIG. 6 is an internal view of the shield according to FIG. 1 illustrating pads, which prevent the shield from rubbing against the SCBA mask lens within the main field of view.

The shield 01 can be attached to the mask 07 using two or more elastic cords, straps, etc. and/or tabs, hooks 06 that use pressure to attach to any part of the mask frame 03 or any other component of the mask 07 as seen in FIGS. 4-6. This means of attachment allows the user unlimited reapplications. The shield 01 will be held securely in place but the user can easily and quickly remove the shield 01 from the mask 07 prior to using the mask 07 in the field or leave it in place for training exercises and for protection while not in use. It is also noted that FIG. 6 illustrates the shield from the inside which is the surface that would abut against the lens.

Figure 3:
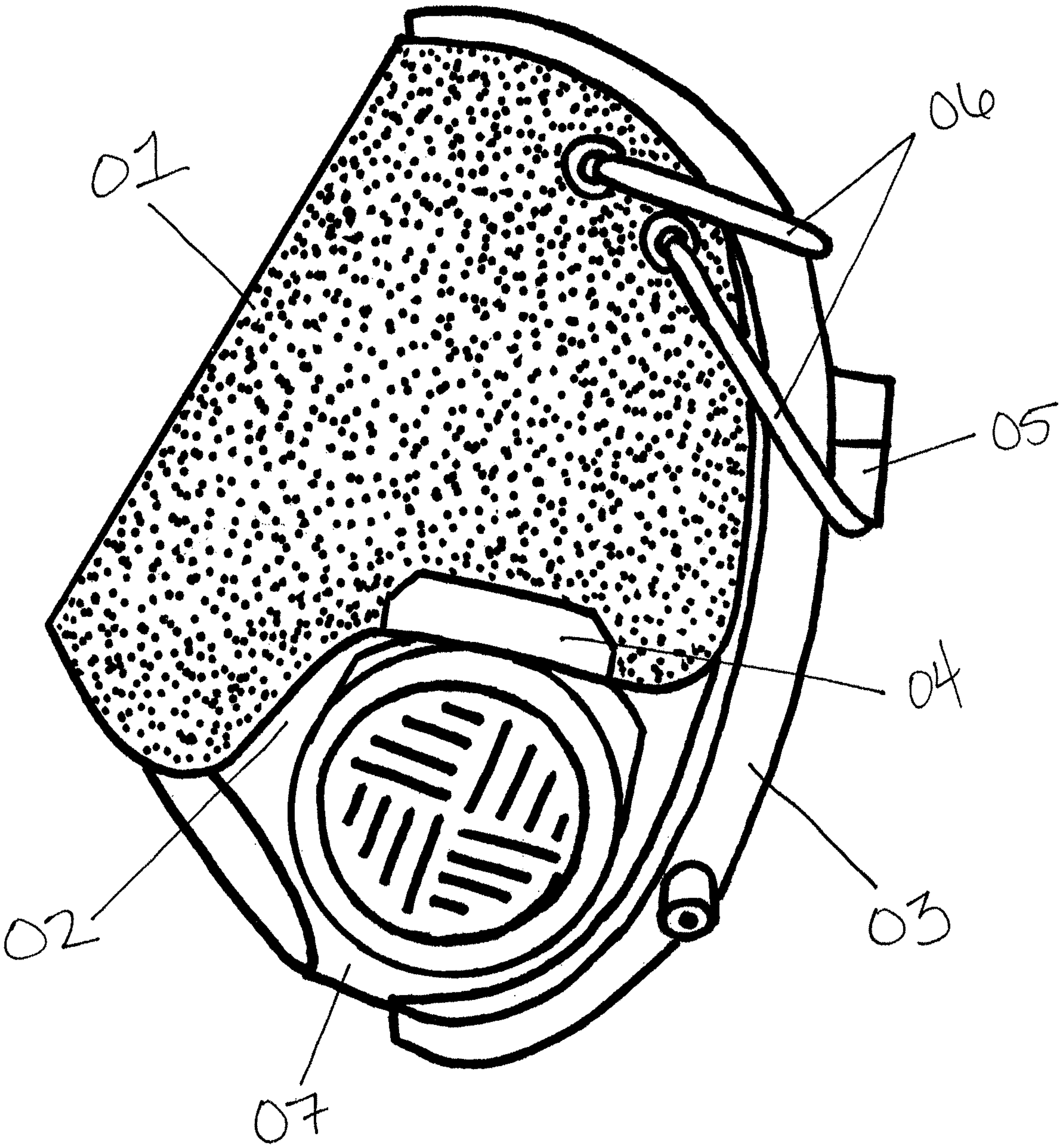
FIG. 3 is a side view of the combination mask and shield according to FIG. 1.

The installation of the shield 01 to the mask 07 is easy to accomplish and understand as shown in FIG. 3-4. The shield 01 is fit to the specific shape of each model of mask 07 and will self-position when the straps, cords, hooks, etc. 06 are secured to the predetermined locations 05 on the mask 07 and the shield 01 will remain in place.

Figure 7:
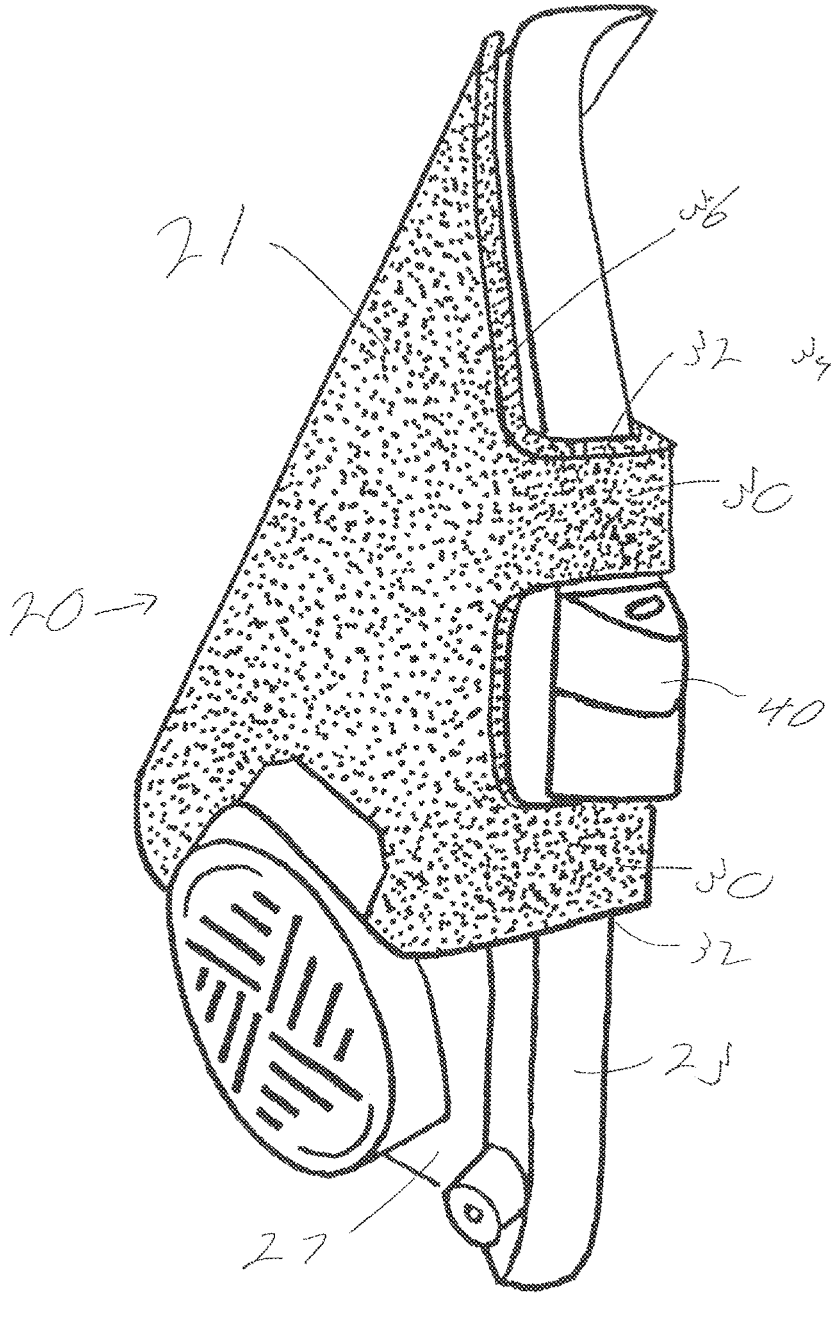
FIG. 7 is a rear and side view of an alternative embodiment of a mask according to principles of the present invention and is shown attached to a commercially manufactured masked.
Figure 8:
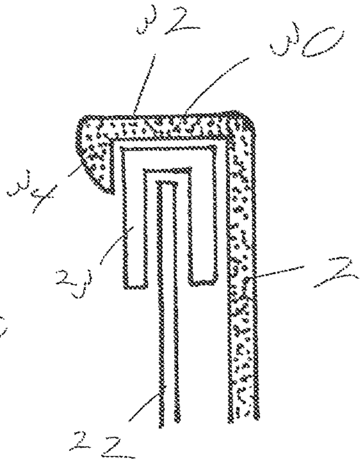
FIG. 8 is a sectional view of a portion of the combination mask and shield according to FIG. 7.

Now referring to FIGS. 7 and 8, an alternative shield 20 is shown attached to a mask 27 by a hook construction 30. The shield 20 is similar to the shield 01 except for the presence of hook construction 30 that extend from sides of the shield 20 and wrap the frame 23 that holds the lens 22. The hook construction 30 includes a flange 32 that extends away from the lens covering portion 21 of the shield 20 and includes a catch 34 that wraps around the frame 23. As shown in FIG. 7, the flanges 32 extend from the first side 36 of the shield 20 on both sides of the clamp 40 of the mask 27. It should be appreciate that the opposite side can be provided as a mirror image and includes flanges and catches that wrap the frame 23. One attaching or detaching the shield 20 to the mask 27 can permit the hooks construction 30 to flex and snap fit over the frame 23 when attaching, and can be pulled back to permit detaching the shield 20 from the mask 27. It is noted that the clamp 40 can be present to clamp the pieces of the frame 23 around the lens 22. Certain masks may not include a clamp, and certain other masks that include a clamp may locate the clamp at a different position. Although the shield 20 is shown having flanges 32 extending on both sides of the clamp 40, it is possible for the shield 20 to have a flange extending on only one side of the clamp 40. Furthermore, when a clamp is not present, the shield can have one or more flanges on each side for wrapping around and attaching to the mask 27.

The hook construction 30 can be provided as an integral part of the shield 20 extending from the lens covering portion 21. By "integral," it is meant that the hook construction 30 is formed from the same material as the lens covering portion 21 and is not separately attached. It should be appreciated, however, that the hook construction 30 can be provided as non-integral with the lens covering portion 21. For example, the hook construction 30 can be adhered or welded to the lens covering portion 21.

While the invention has been described in complete detail and pictorially shown in the provided drawings, it is not to be limited to such details, since many changes and modifications may be made to the invention without departing from the spirit and scope thereof. Hence, it is described to cover any and all modifications and forms, which may come within the language and scope of the appended claims.

What is claimed is:

1. A combination mask and shield comprising:

(a) a mask provided as part of a self-contained breathing apparatus and including a lens and a frame holding the lens in place; and (b) a shield constructed to cover an exterior surface of the lens and also cover the frame holding the lens in place, the shield comprising:

(i) a cover having an inside surface, an outside surface, a perimeter corresponding to a perimeter of the frame holding the lens, and a contour configured to follow a contour of the lens; and (ii) a first elastic cord extending from a first part of the cover and a second elastic cord extending from a second part of the cover, and wherein the first elastic cord and the second elastic cord interact with the mask to hold the shield over the lens.

2. A combination mask and shield according to claim 1 wherein:

(a) the cover comprises a plastic material.

3. A combination mask and shield according to claim 2 wherein:

(a) the plastic material comprises a thermoplastic material having a thickness of 1 to 15 mm.

4. A combination mask and shield according to claim 2 wherein:

(a) the plastic material comprises polyethylene, cellulose acetate, polycarbonate, acrylic, acetyle, or polyester.

5. A combination mask and shield according to claim 2 wherein:

(a) the plastic material is die cut.

6. A combination mask and shield according to claim 2 wherein:

(a) the cover is formed by injection molding the plastic material.

7. A combination mask and shield according to claim 1 wherein:

(a) the cover comprises a light blocking plastic material.

8. A combination mask and shield according to claim 1 wherein:

(a) the cover comprises a translucent plastic material.

9. A combination mask and shield according to claim 1 wherein:

(a) the first elastic cord and the second elastic cord extend through a portion of the cover and attach to a portion of the mask to thereby hold the cover over the lens when the cover is located covering the lens.

10. A combination mask and shield according to claim 1 wherein:

(a) the shield further comprises a separation member located on the inside surface of the cover and providing separation between the lens and the cover, wherein the separation member comprises a plurality of discrete members located on the cover inside surface along the perimeter corresponding to the perimeter of the frame holding the lens.

11. A combination mask and shield according to claim 10 wherein:

(a) the separation member comprises felt, suede, or rubber.

* * * * *